United States Patent [19]

Janusz et al.

[11] Patent Number: 4,677,126

[45] Date of Patent: Jun. 30, 1987

[54] OXA-FENCHYL ESTERS AND AMIDES OF ALPHA-L-ASPARTYL-D-PHENYLGLYCINE

[75] Inventors: John M. Janusz, Fairfield; John M. Gardlik, Cincinnati, both of Ohio

[73] Assignee: The Procter & Gamble Company, Cincinnati, Ohio

[21] Appl. No.: 909,743

[22] Filed: Sep. 19, 1986

Related U.S. Application Data

[63] Continuation of Ser. No. 630,457, Jul. 13, 1984, abandoned.

[51] Int. Cl.$^4$ .................... A61K 37/02; C07C 10/30; C07C 10/22
[52] U.S. Cl. .................................. 514/19; 560/39; 560/41; 562/444; 562/449; 562/450
[58] Field of Search ................ 260/998.2; 560/39, 41; 562/444, 449, 450; 514/19

[56] References Cited

U.S. PATENT DOCUMENTS 3,972,860  8/1976  Moriarty et al. .................... 426/548
4,399,163  8/1983  Brennan et al. .................... 426/548

FOREIGN PATENT DOCUMENTS 0175470  10/1983  Japan.

OTHER PUBLICATIONS

Goodman et al., *Proc. 15th Eur. Pep. Symp.*, 271–278, (1974).

*Primary Examiner*—Johnnie R. Brown
*Assistant Examiner*—F. T. Moezie
*Attorney, Agent, or Firm*—David K. Dabbiere; Eric W. Guttag; Steven J. Goldstein

[57] ABSTRACT

Oxa-fenchyl esters and amides of alpha-L-aspartyl-D-phenylglycine are disclosed to be useful as high intensity sweeteners. These compounds can be used to sweeten a variety of foods, beverages and other oral products.

9 Claims, No Drawings

OXA-FENCHYL ESTERS AND AMIDES OF ALPHA-L-ASPARTYL-D-PHENYLGLYCINE

This is a continuation of application Ser. No. 630,457, filed on July 13, 1984, now abandoned.

TECHNICAL FIELD

The present application relates to oxa-fenchyl and like esters and amides of alpha-L-aspartyl-D-phenylglycine useful as high intensity sweeteners.

Sweeteners are used in a variety of orally ingested products. For example, sweeteners are an important component of cakes, cookies, chewing gum, dentifrices and the like. Sweeteners are a particularly important ingredient in beverages. In terms of volume, carbonated beverages use more sweeteners than any other sweetened product category.

The most widely used sweetener for food, and especially beverage products, is sucrose. Sucrose is safe, naturally occurring, and has a high sweetness quality in terms of a pure, quick onset of sweetness with no aftertaste or undertaste. However, the normal usage of sucrose provides significant caloric load which is undesirable for those persons on weight control or reduction programs. Also, those persons who have diabetes must carefully control their intake of sucrose to avoid problems associated with the disease. Sucrose is also cariogenic so that it cannot be used in dentifrices and is undesirable in chewing gums. Additionally, and perhaps little realized, for the amount of sweetness delivered, sucrose can be expensive relative to other sweeteners such as saccharin, especially when used in carbonated beverages.

The drawbacks of sucrose, including its expense, have led those in the beverage industry to seek substitute sweeteners. One particularly important quality sought in such sweeteners is high sweetness intensity. Sweetness intensity can affect not only the safety profile and caloric value of the sweetener, but also its cost in terms of sucrose equivalent sweetness. However, the inability to predict that a given compound is sweet, and particularly that it has high sweetness intensity, makes the search for suitable substitute sweeteners a "hit-or-miss" proposition.

Such unpredictability is especially true for the currently popular L-aspartic acid derived sweeteners represented by the following formula:

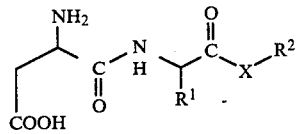

where X is O (ester) or NH (amide). Various theories have been proposed for what imparts sweetness to these particular molecules. However, the current belief is that groups $R^1$ and $R^2$ need to be dissimilar in size for greatest sweetness intensity, i.e. one group large or bulky, the other group small. See Goodman et al., "Peptide Sweeteners: A Model for Peptide and Taste Receptor Interactions," *Proc.* 15th *Eur. Pep. Symp.*, (1974), pp. 271–78; Sukehiro et al., "Studies on Structure-Taste Relationships of Aspartyl Peptide Sweeteners: Syntheses and Properties of L-Aspartyl-D-Alanine Amides," *Science of Human Life*, Vol. 11, (1977), pp. 9–16. It also appears that when $R^1$ is the large or bulky group, the stereochemical configuration generally needs to be L, L for sweetness. See U.S. Pat. No. 3,972,860 to Moriarty et al., issued Aug. 3, 1976 (L-aspartyl-L-phenylglycine lower alkyl esters are sweet); U.S. Pat. No. 3,492,131 to Schlatter, issued Jan. 27, 1970 (L-aspartyl-L-phenylalanine lower alkyl esters are sweet). Conversely, when $R^1$ is the small group, the stereochemical configuration generally needs to be L, D for sweetness. See U.S. Pat. No. 4,411,925 to Brennan et al., issued Oct. 25, 1983 (L-aspartyl-D-alanine amides are sweet); Ariyoshi et al., "The Structure-Taste Relationships of the Dipeptide Esters Composed of L-Aspartic Acid and Beta-Hydroxyamino Acids," *Bull. Chem. Soc. Jap.*, Vol. 47, (1974), pp. 326–30 (L-aspartyl-D-serine esters are sweet). Even with these guidelines, the sweetness intensity of these L-aspartic acid derived sweeteners can vary greatly depending upon which combination of $R^1$ and $R^2$ groups are selected. Compare U.S. Pat. No. 4,411,925, supra (X is NH, $R^1$ is methyl group, $R^2$ is 2,6-dimethyl cyclohexyl group, sweetness intensity is 600 times that of sucrose), with U.S. Pat. No. 3,907,766 to Fujino et al., issued Sept. 23, 1975 (X is O, $R^1$ is methyl ester group, $R^2$ is fenchyl group, sweetness intensity is 22,200–33,200 times that of sucrose).

For beverage use, the substitute sweetener must be sufficiently soluble and hydrolytically stable. Most carbonated beverages have a pH of from about 2.5 to about 4.8. Useful sweeteners in such beverages must therefore be relatively resistant to acid catalyzed breakdown. Otherwise, the beverage can quickly lose its sweetness or possibly have undesirable off-flavors imparted to it. As in the case of sweetness intensity, it can be difficult to predict whether a given sweetener will be hydrolytically stable, especially in an acidic environment.

Other factors are also important in providing a useful substitute sweetener. To obtain approval for food or beverage use, the substitute sweetener must be safe in terms of acute toxicity as well as long-term effects from continued use. The substitute sweetener should also desirably approach sucrose in terms of sweetness quality, as well as have a relatively quick onset and short duration of sweetness. Finally, to be classified as a non-caloric sweetener, the substitute sweetener (or metabolic products thereof) should provide minimal or no caloric value at normal usage levels.

The most widely used substitute sweetener at present is saccharin, in particular its sodium salt. Saccharin has a relatively high sweetness intensity (about 300 times that of sucrose) and is relatively inexpensive in providing sucrose equivalent sweetness in carbonated beverages. However, saccharin also provides an undesirable lingering bitter aftertaste.

Besides saccharin, a number of the L-aspartic acid derived amides have been proposed as suitable substitute sweeteners. The most prominent examples are the alpha-L-aspartyl-L-phenylalanine lower alkyl esters, in particular the methyl ester known as aspartame. Aspartame has been approved for use in dry foods and beverages, and has recently been approved for use in aqueous beverage systems such as carbonated beverages. The sweetness intensity of aspartame is about 150-200 times that of sucrose with a sweetness quality approaching that of sucrose. The caloric value of aspartame is also relatively minimal at normal usage levels. However, aspartame is hydrolytically unstable in most carbonated beverages. Perhaps more important to the beverage industry, aspartame is extremely expensive in terms of sucrose equivalent sweetness delivered.

The search therefore continues for substitute sweeteners which are (1) inexpensive in terms of sucrose equivalent sweetness; (2) are hydrolytically stable in carbonated beverage systems; (3) are safe; (4) have satisfactory taste quality; and (5) provide minimal caloric value.

BACKGROUND ART

A. L-aspartyl-L-phenylglycine esters

U.S. Pat. No. 3,972,860 to Moriarty et al., issued Aug. 3, 1976, discloses L-aspartyl-L-phenylglycine lower alkyl ester sweeteners. The preferred methyl ester is disclosed as having a sweetness intensity of from 100–1000 times that of sucrose. See also Goodman et al., "Peptide Sweeteners: A Model for Peptide and Taste Receptor Interactions," *Proc.* 15th *Eur. Pep. Symp.,* (1974), pp. 271–78, which discloses that the methyl ester of L-aspartyl-L-phenylglycine is "quite sweet."

B. Peptides Containing D-phenylglycine

U.S. Pat. No. 4,183,909 to Schon et al. issued Jan. 15, 1980, discloses phenylglycine-containing peptides which greatly increase gastric acid secretion when administered intravenously. One of the precursors of these peptides is the beta-tert-butyl ester of L-aspartyl-L-phenylglycine hydrochloride (Example 1, Step 4).

C. L-aspartyl-D-alanine amides

U.S. Pat. No. 4,411,925 to Brennan et al. issued Oct. 23, 1983, discloses L-apartyl-D-alanine amide sweeteners. These amides have the formula:

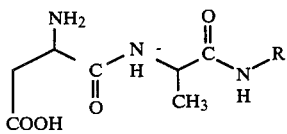

wherein R is a branched hydrocarbyl group, including fenchyl (320 times as sweet as sucrose). The highest intensity sweeteners include those where R is 2,5 dimethylcyclopentyl (520 times that of sucrose), 2,6-dimethylcyclohexyl (600 times that of sucrose), dicyclopropylcarbinyl (1200 times that of sucrose) 2,2,4,4-tetramethylthietan-3-yl (2000 times that of sucrose), or 2,2,4,4-tetramethyl-1,1-dioxothietan-3-yl (1000 times that of sucrose). See also Sukehiro et al., "Studies on Structure-Taste Relationships of Aspartyl Peptide Sweeteners: Syntheses and Properties of L-Aspartyl-D-Alanine Amides," *Science of Human Life,* Vol. 11, (1977), pp. 9–16, which discloses L-aspartyl-D-alanine amide sweeteners (10 to 125 times that of sucrose) wherein R is $C_2$–$C_4$ alkyl or cyclohexyl.

D. L-aspartyl-aminomalonic acid diesters

U.S. Pat. No. 3,907,766 to Fujino et al., (assigned to Takeda Chemical Industries, Ltd.), issued Sept. 23, 1975 discloses L-aspartyl-aminomalonic diester sweeteners. These diesters have the formula:

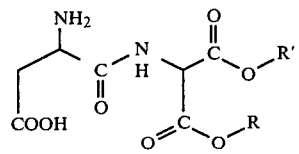

wherein R' is fenchyl and R is methyl (22,200–33,200 times that of sucrose) or ethyl (4200–5400 times that of sucrose). Fujino et al., "Structure-Taste Relationships of L-aspartyl-aminomalonic Acid Diesters," *Chem. Pharm. Bull.,* Vol. 24 (1976), pp. 2112–17, suggests that the L-aspartyl-L-aminomalonic acid diester is the sweet one. See page 2116. See also U.S. Pat. No. 3,801,563 to Nakajima et al. (assigned to Takeda Chemical Industries, Ltd.), issued Apr. 2, 1974, which discloses other L-aspartyl-aminomalonic acid diesters containing branched or cyclic alkyl ester groups.

E. L-aspartyl-D-amino acid esters

Mazur et al., "Synthetic Sweeteners: Aspartyl Dipeptide Esters from L- and D-alkylglycines," *J. Med. Chem.,* Vol. 16, (1973), pp. 1284–87, discloses sweetness intensity testing of isopropyl esters of L-aspartyl-D-amino acids. These esters have the formula:

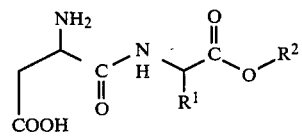

wherein $R^2$ is isopropyl and $R^1$ is a $C_1$–$C_4$ alkyl group. The sweetness intensity of the particular esters ranges from 0–170 times that of sucrose.

Ariyoshi et al., "The Structure-Taste Relationships of the Dipeptide Esters Composed of L-aspartic Acid and Beta-hydroxyamino Acids," *Bull. Chem. Soc. Jap.,* Vol. 47, (1974), pp. 326–30, discloses sweetness intensity testing of $C_1$–$C_4$ alkyl or cyclohexyl esters of L-aspartyl-D-amino acids. These esters have the formula:

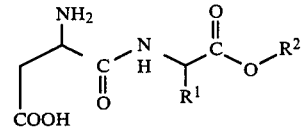

wherein $R^2$ is a $C_1$–$C_4$ alkyl or cyclohexyl group, and $R^1$ is a $C_1$–$C_2$ alkyl or hydroxyalkyl group. The D-amino acids used include D-serine ($R^1$=hydroxymethyl); D-threonine ($R^1$=hydroxyethyl), D-allo-threonine ($R^1$=a-hydroxyethyl), and D-2-aminobutyric acid ($R^1$=ethyl). The sweetness intensity of the particular esters can range from 6–320 times that of sucrose.

Ariyoshi "The Structure-Taste Relationships of Aspartyl Dipeptide Esters," *Agr. Biol. Chem.,* Vol. 40, (1976), pp. 983–92, discloses sweetness intensity testing of $C_1$–$C_3$ alkyl or cyclohexyl esters of L-aspartyl-D-amino acids. These esters have the formula:

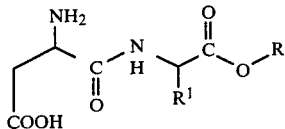

wherein R is a $C_1$-$C_3$ alkyl or cyclohexyl group, and $R^1$ is a $C_1$-$C_3$ alkyl or hydroxyalkyl, or benzyl group. The methyl ester of L-aspartyl-D-phenylalanine is disclosed to be bitter.

See also U.S. Pat. No. 3,492,131 to Schlatter (assigned to G. D. Searle & Co.), issued Jan. 27, 1970, which states that the L-aspartyl-D-phenylalanine esters are not sweet.

DISCLOSURE OF THE INVENTION

The present invention relates to certain alpha-L-aspartyl-D-phenylglycine esters and amides useful as sweeteners. These esters and amides include the non-toxic salts and have the formula:

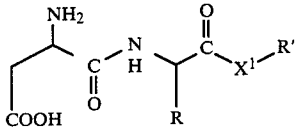

wherein the ester or amide is the L,D stereochemical isomer; wherein $X^1$ is O or NH; wherein R is a phenyl group having the formula:

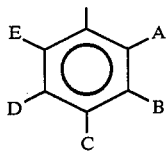

wherein A, B, C, D and E are H, OH, F, Cl, Br, or $C_1$–$C_4$ alkyl, hydroxyalkyl or alkoxy; and wherein R' is selected from the group consisting of bicyclic radicals having formulas (a) (b) and (c):

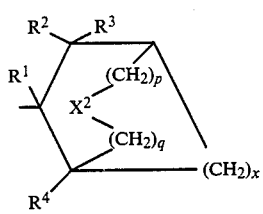

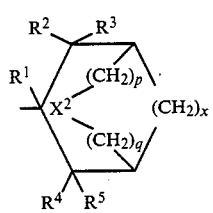

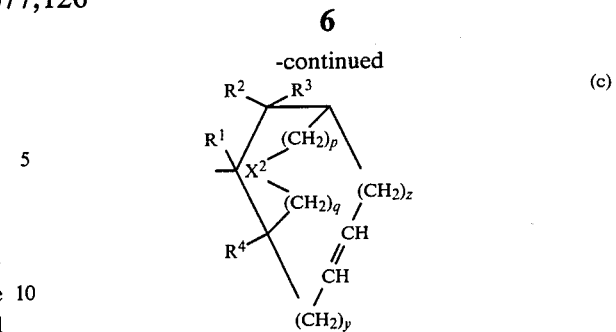

wherein $R^1$, $R^2$, $R^3$, $R^4$ and $R^5$ are H, or $C_1$-$C_4$ alkyl, hydroxyalkyl or alkoxy; provided that at least one of $R^2$, $R^3$, $R^4$ and $R^5$ are $C_1$-$C_4$ alkyl, hydroxyalkyl or alkoxy, $X^2$ is O; p and q are 0, 1, 2 or 3 and the sum of p+q is not greater than 3; x is 1, 2 or 3; y and z are 0, 1 or 2 and the sum of y+z is not greater than 2.

These alpha-L-aspartyl-D-phenylglycine esters and amides are more hydrolytically stable in carbonated beverages than aspartame. Also, certain of these esters and amides have sufficiently high sweetness intensity so as to be relatively inexpensive in terms of sucrose equivalent sweetness. Based on available data for the expected metabolites, it is believed that these esters and amides are safe for use in food and beverage systems, and will provide minimal caloric value at normal usage levels. The taste quality of these sweeteners is also satisfactory.

A. Alpha-L-aspartyl-D-phenylglycine esters and amides

The esters and amides of the present invention have the formula:

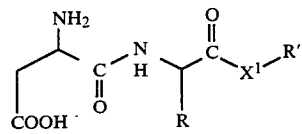

It has been determined that the L,D stereochemical isomer imparts the sweetness character to these esters and amides. However, minor amounts of the D,L, L,L and D,D stereochemical isomers can be tolerated without adversely affecting the taste quality of L,D stereochemical isomer. Such diastereomeric mixtures typically comprise at least about 50% of the L,D stereochemical isomer, preferably at least about 70% of the L,D isomer, and most preferably at least about 95% of the L,D isomer.

The esters or amides of the present invention can be in the form of non-toxic salts. As used herein, "non-toxic salts" means salts of the present esters and amides which are physiologically acceptable for ingestion. Such salts include both cationic and acid addition salts of these esters and amides. By "cationic salts" is meant those salts formed by neutralization of the free carboxylic acid group of the instant esters and amides by bases of physiologically acceptable metals, ammonia and amines. Examples of such metals are sodium, potassium, calcium and magnesium. Examples of such amines are n-methyl-glucamine and ethanolamine. By "acid addition salts" is meant those salts formed between the free amino group of the instant esters and amides and a physiologically acceptable acid. Examples of such acids are acetic, benzoic, hydrobromic, hydrochloric, citric, fumaric, gluconic, lactic, maleic, malic, sulfuric, sulfonic, nitric, phosphoric, saccharic, succinic and tartaric acids.

The compounds of the present invention can be in the form of either esters or amides ($X^1$ is O or NH). The amides are desirable from the standpoint of having greater hydrolytic stability than the esters. However, the esters have acceptable hydrolytic stability and in particular have a hydrolytic stability greater than that of aspartame. Also, in terms of sweetness intensity, the esters tend to have a greater sweetness intensity.

The phenyl group R of the esters or amides of the present invention has the formula:

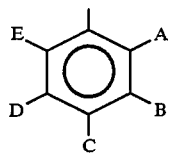

wherein A, B, C, D and E are H, OH, F, Cl, Br or $C_1$–$C_4$ alkyl, hydroxyalkyl or alkoxy. Preferred groups R are those where A, B, C, D and E are all H or where one of A, B, C, D and E is OH or F. Particularly preferred groups R are phenyl (A, B, C; D and E are H), p-hydroxyphenyl (C is OH; A, B, D and E are H) and o-fluorophenyl (A is F; B, C, D and E are H).

The terminal group R' can be selected from a variety of bicyclic radicals. The first group of such radicals have the formula (a):

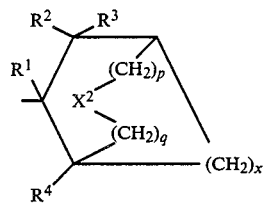

wherein $R^1$, $R^2$, $R^3$, and $R^4$ are H or $C_1$–$C_4$ alkyl, hydroxyalkyl or alkoxy; provided that at least one of $R^2$, $R^3$ and $R^4$ are $C_1$–$C_4$ alkyl, hydroxyalkyl or alkoxy; $X^2$ is O; p and q are each 0, 1, 2 or 3; the sum of p+q being not greater than 3; and x is 1, 2 or 3. Preferably $R^2$, $R^3$ and $R^4$ are methyl or H; $R^1$ is preferably H; the sum of p+q is preferably 0; x is preferably 2. Especially preferred radicals of formula (a) are alpha-7-oxa-fenchyl and beta-7-oxa-fenchyl.

A second set of such radicals have the formula (b):

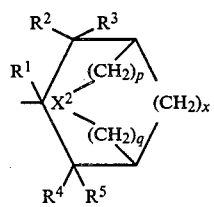

wherein $R^1$, $R^2$, $R^3$, $R^4$, $X^2$, p, q and x are defined as before; and $R^5$ is H or $C_1$–$C_4$ alkyl, hydroxyalkyl, or alkoxy. Preferably $R^2$, $R^3$, $R^4$ and $R^5$ are methyl or H; $R^1$ is preferably H; the sum of p+q is preferably 0; x is preferably 2.

A third set of such radicals have the formula (c):

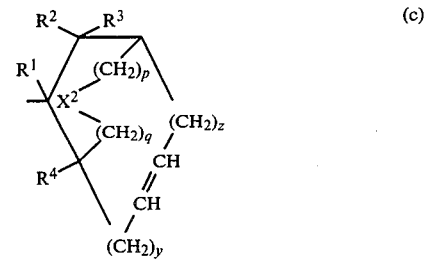

wherein $R^1$, $R^2$, $R^3$, $R^4$, $X^2$, p and q are defined as before; and y and z are 0, 1 or 2 and the sum of y+z is no greater than 2. Preferably, $R^2$, $R^3$ and $R^4$ are H or methyl; $R^1$ is preferably H; the sum of p+q is preferably 0; the sum of y+z is preferably 0 or 1.

B. Sweetness Intensity of Alpha-L-Aspartyl-D-Phenylglycine Esters and Amides

The sweetness intensity of the esters and amides of the present invention relative to sucrose can be determined according to the following procedure:

Male subjects are chosen at random from a group of about 20 persons who have previously been selected on the basis of proven tasting acuity, i.e., persons who could easily recognize the four basic tastes (sweet, sour, bitter and salty) and who are adept at quantifying their own physiological response numerically. The subjects are asked to taste and expectorate about 10 ml of a test sample (temperature of about 22° C.) having dissolved therein the ester or amide. The subjects are then asked to compare the sweetness of the test sample with five standard samples which contain increasing amounts of sucrose. The standard samples are letter coded A, B, C, D and E and are designated on a ballot by a closed linear scale. Sweetness intensity of the test sample is recorded by the subject making a mark on the linear scale at a point he considers equal in sweetness among the standard samples; interpolation between standards is encouraged. After completion of the panel, a five point numeric scale is superimposed on the linear scales to obtain numerical data; data is averaged and recorded to the nearest 0.25 unit. Equivalent sucrose sweetness is determined by referring to graphs of (w/v) sucrose concentration in the standard samples versus a linear numeric scale.

Sweetness intensity is calculated by dividing the concentration (w/v) of perceived sweetness by the concentration (w/v) of the ester or amide required to produce that sweetness. The five point scale with standard samples ranging from 1.37% (0.040M) to 11.97% (0.35M) sucrose is used for sweetness intensity testing. The test sample is prepared at a concentration which would be equal to about 8–10% sucrose.

The sweetness intensity of the esters and amides of the present invention is presented in the following table:

| R Group | Type | R' Group | Sweetness (× Sucrose) |
|---|---|---|---|
| Phenyl | Ester | alpha-7-oxa-fenchyl | 1000* |

*based on informal panel testing

Synthesis of alpha-L-aspartyl-D-phenylglycine esters and amides

The alpha-L-aspartyl-D-phenylglycine esters of the present invention can be synthesized according to the following 4-step reaction scheme:

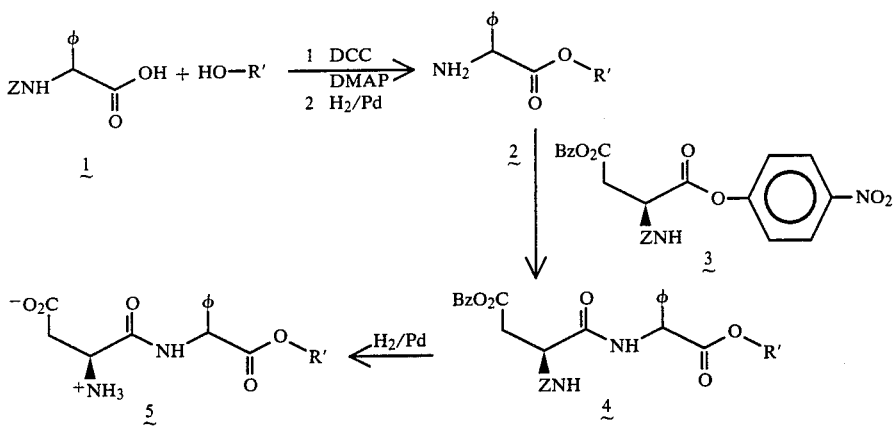

In the first step, carbobenzyloxy (Z) protected D-phenylglycine 1 is coupled with alcohol R'OH using dicyclohexylcarbodiimide (DCC)/dimethylaminopyridine (DMAP). In the second step, the ester formed in step 1 is hydrogenated over palladium to remove the protecting group to form the phenylglycine ester 2. In the third step, ester 2 is coupled to the protected activated L-aspartic ester 3 to form the protected L-aspartyl-D-phenylglycine ester 4. In the fourth step, the protecting groups are removed by hydrogenation of ester 4 over palladium to yield sweetener 5.

Alcohols R'OH used in this synthesis are made according to the process disclosed in U.S. application Ser. No. 630,464 to John M. Cardik, filed July 13, 1984 (Case 3295) (herein incorporated by reference). This process involves the following 4-step reaction scheme:

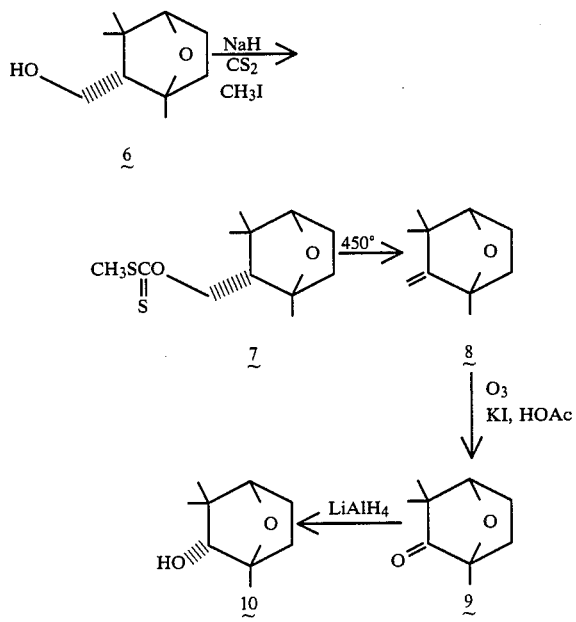

In the first step, alcohol 6 is converted to the xanthate ester 7 by using NaH, carbon disulfide and methyl iodide. In the second step, xanthate ester 7 is thermally decomposed to the methylene substituted bicyclic compound 8. In the third step, bicyclic compound 8 is converted to ketone 9 by using ozone, KI and acetic acid. In the fourth step, ketone 9 is reduced to alcohol 10.

Syntheses of specific alpha-L-aspartyl-D-phenylglycine esters are as follows:

EXAMPLE 1: alpha-7-oxa-Fenchyl ester

Step 1

N-Carbobenzyloxy-D-phenylglycine-(±)-alpha-7-oxa-fenchyl ester a. N-Carbobenzyloxy-D-phenylglycine

To D-phenylglycine (50 g., 0.33 moles, Aldrich) is added 82 ml. of 4N NaOH. The mixture is cooled to 0° C. and carbobenzoxy chloride (51 ml., 0.36 moles) is added dropwise. Additional NaOH is added as needed to keep the reaction mixture basic. After stirring for 10 minutes, 200 ml. of H$_2$O is added. After 10 minutes, the solution is filtered. The clear filtrate is extracted twice with ether and is then adjusted to pH 3 with 5N HCl. The resulting precipitate is filtered, washed twice with H$_2$O and then dried. The crude product is dissolved in ethyl acetate and then filtered. The filtrate is evaporated and the resulting solid crystallized from ethyl acetate/hexane.

b. (±)-alpha-7-oxa-Fenchol (±)-alpha-7-oxa-Fenchol is prepared according to the procedure of Example 2, Step 1b.

c. N-Carbobenzyloxy-D-phenylglycine-(±)-alpha-7-oxa-fenchyl ester

The N-carbobenzyloxy-D-phenylglycine (20 g., 0.07 moles) from step 1a is dissolved in about 150 ml. of dry methylene chloride. The (±)-alpha-7-oxa-fenchol (10.9 g., 0.07 moles) from step 1b and N,N'-dicyclohexylcarbodiimide (17.3 g., 0.083 moles) are then added after cooling the solution to 0° C. The mixture thickens; additional methylene chloride (about 150 ml.) is added. When the mixture becomes more uniform, it is then chilled to −65° C. 4-Dimethylaminopyridine is then added and the mixture stirred at −60° to −65° C. for 1 hour. The cooling bath is then changed to carbon tetrachloride/dry ice to maintain the mixture at −23° C. for 3 hours. The precipitated N,N'-dicyclohexylurea is filtered off. The filtrate is successively washed with chilled H2O, 0.1N HCl, 2% NaHCO3, H2O and brine. The filtrate is dried over MgSO4, filtered and then evaporated.

Step 2: D-Phenylglycine-(±)-alpha-7-oxa-fenchyl ester

To a Parr flask is added 5% palladium on charcoal (200 mg.). The crude ester (28.8 g.) from step 1c in about 200 ml. of methanol is then added. The contents of the flask are hydrogenated for 5 hours. Additional 5% palladium on charcoal (200 mg.) plus 10% palladium on charcoal (100 mg.) is added to the flask and hydrogenation is continued overnight. The contents of the flask are then filtered and evaporated to yield the crude product. This crude product is dissolved in 0.1N HCl and is extracted twice with ether to remove non-basic impurities. The aqueous layer is adjusted to pH 9-10 with NaOH and is then extracted 3 times with ether. The combined extracts are successively washed with H2O and brine, and then dried over MgSO4. The dried extracts are filtered and then evaporated to give the desired ester.

Step 3 beta-Benzyl-N-carbobenzyloxy-L-aspartyl-D-phenylglycine-(±)-alpha-7-oxa-fenchyl ester a.
beta-Benzyl-N-carbobenzyloxy-L-aspartyl-p-nitrophenyl ester To a 1000 ml. 3-neck flask is added beta-benzyl-N-carbobenzyloxy-L-aspartic acid (50 g., 0.14 moles, Bachem Inc.), p-nitrophenol (23.5 g., 0.17 moles) and about 350 ml. of ethyl acetate. This mixture is stirred and then 4-dimethylaminopyridine (1.0 g.) and N,N'-dicyclohexylcarbodiimide (28.5 g., 0.14 moles) is added. The solution becomes warm; after 4 hours, the reaction is complete as measured by thin layer chromatography. The solution is then filtered to remove precipitated N,N'-dicyclohexylurea and then extracted 9 times with saturated Na2CO3 solution, then 2 times with saturated NaCl solution. The extracted solution is dried over Na2SO4 and then concentrated to yield the crude ester. This concentrated solution is dissolved in hot ethanol and then seeded. The concentrated solution is allowed to fully crystallize at room temperature and is then cooled with ice. The crystals are filtered and then washed with cold ethanol.

b.
beta-Benzyl-N-carbobenzyloxy-L-aspartyl-D-phenylglycine-(±)-alpha-7-oxa-fenchyl ester The p-nitrophenyl ester from step 3a (19.6 g., 0.041 moles) is dissolved in 100 ml. of dry tetrahydrofuran (THF) and is chilled to 0° C. The 7-oxa-fenchyl ester from step 2 (11.8 g., 0.041 moles) is added and the reaction mixture is then stirred at 0° C. for 1 hour. The reaction mixture is stirred overnight at room temperature and then the THF is evaporated. The residue is partitioned between ethyl acetate and H2O. The organic layer is successively washed with cold 10% Na2CO3, H2O, and brine, and then dried over MgSO4. The dried solution is filtered and then evaporated to give the crude product. This crude product is purified by silica gel chromatography first with 2% acetone/chloroform solvent and then with 25% ethyl acetate/hexane solvent.

Step 4:
alpha-L-Aspartyl-D-phenylglycine-(−)-alpha-7-oxafenchyl ester

The purified ester from step 3b (7 g., 0.011 moles) is dissolved in 150 ml. of methanol and is then hydrogenated over 5% palladium on charcoal (300 mg.) for 22 hours. A second portion of the purified ester from step 3b (8 g., 0.013 moles) is hydrogenated over 10% palladium on charcoal (300 mg.) for 5 hours. The catalyst is filtered off and the solvent evaporated for a combined yield of the desired sweetener.

In certain instances, use of carbobenzyloxy protected D-phenylglycine can cause partial racemization at the asymmetric carbon of the phenylglycine moiety during formation of ester 2. Racemization can be minimized by using o-nitrophenylsulfenyl (o-Nps) protected D-phenylglycine to form ester 2 according to the following reactions:

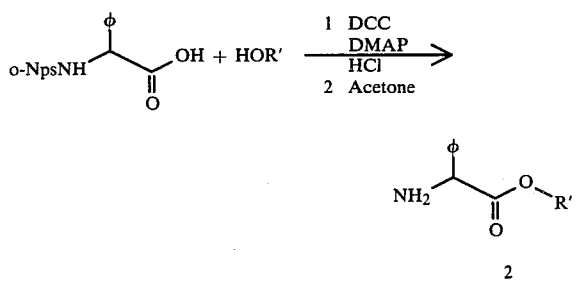

Ester 2 can be converted to the desired ester 5 by the previously described procedure.

Synthesis of specific esters 5 using o-nitrophenylsulfenyl protected D-phenylglycine are as follows:

EXAMPLE 2: alpha-7-oxa-Fenchyl ester

Step 1:
o-Nitrophenylsulfenyl-D-phenylglycine-(±)-alpha-7-oxafenchyl ester a: o-Nitrophenylsulfenyl-D-phenylglycine D-phenylglycine (51 g., 0.34 moles, Aldrich) was dissolved in 180 ml. of 2N NaOH and 200 ml. of dioxane. Then o-nitrophenylsulfenyl chloride (64 g., 0.34 moles) was added in small portions over 1 hour with simultaneous addition of 180 ml. of 2N NaOH. The reaction mixture was stirred for 2 hours and then diluted with 500 ml. of H2O. The mixture was filtered and the solids washed with H2O. The filtrate was acidified with H2SO4 and then extracted 3 times with ether. The combined extracts were successively washed with H2O and brine, dried over Na2SO4 and then evaporated. The crude product was then recrystallized from ethyl acetate/hexane. Yield: 64.5 g. The purified product was characterized by NMR. $[\alpha]_D = -179.5°$ (C 0.4, methanol).

b: (±)-alpha-7-oxa-Fenchol (1):
(±)-endo-1,3,3-Trimethyl-7-oxabicyclo[2.2.1]heptane-2-methanol Geraniol was converted to (±)-endo-1,3,3-trimethyl-7-oxabicyclo[2.2.1]heptane-2-methanol using thallium (III) perchlorate according to the procedure described in Yamada et al., *J. Chem. Soc. Chem. Comm.*, (1976), page 997.

(2): S-methyl xanthate ester of (±)-endo-1,3,3-trimethyl-7-oxabicyclo[2.2.1]heptane-2-methanol (±)-endo-1,3,3-Trimethyl-7-oxabicyclo[2.2.1]heptane-2-methanol from step (1) (2.1 g, 0.013 moles) was slowly added to a suspension of NaH (0.90 g., 0.038 moles) in 100 ml. of THF at 0° C. under argon. After stirring at 0° C. for 5 minutes, the reaction mixture was refluxed for 2 hours. Carbon disulfide (2.9 g., 0.038 moles) was added dropwise and the reaction mixture was refluxed for 1 hour. Methyl iodide (5.35 g, 0.037 moles) was then added dropwise and the reaction mixture was refluxed for an additional 2 hours. At this point, the reaction mixture was cooled to room temperature, $H_2O$ was slowly added until two phases formed, the layers were separated, and the aqueous layer was extracted with ether. The organic layers were combined, washed successively with $H_2O$ and brine, and then dried over $MgSO_4$. Evaporation of the solvent and vacuum distillation of the residue afforded the xanthate as an amber oil. Yield: 2.78 g. The distilled product was characterized by NMR.

(3): (±)-1,3,3-Trimethyl-2-methylidine-7-oxabicyclo[2.2.1]heptane

The xanthate ester from step (2) (2.78 g, 0.011 moles) was pyrolyzed in the vapor phase at 450° C., 0.1 mm. pressure using a glass tube packed with glass beads heated by a cylindrical furnace. The product was collected using two traps connected in series, both cooled to −78° C. Yield: 1.27 g. The crude product was characterized by NMR.

(4) (±)-1,3,3-Trimethyl-7-oxabicyclo[2.2.1]heptane-2-one

A stream of 3–5% ozone in oxygen was passed through a solution of (±)-1,3,3-trimethyl-2-methylidine-7-oxabicyclo[2.2.1]heptane from step (3) (1.20 g, 0.007 moles) in 35 ml. of methanol at −78° C. until the solution became light blue (ozone saturation). The excess ozone was removed by purging the cold reaction mixture with oxygen for 15 minutes. The cold reaction mixture was then poured onto a stirred solution of 15 ml. of methanol, 4 ml. of glacial acetic acid, and 8 g. of sodium iodide and stirred for 30 minutes. Sodium thiosulfate solution (0.1N) was added to decompose the liberated iodine. Saturated sodium bicarbonate solution was then added until the mixture was slightly basic (pH 7.5). The aqueous mixture was extracted with ether, the extract washed with brine, and then dried over $Na_2SO_4$. Evaporation of the solvent afforded the product which was characterized by NMR. Yield: 1.12 g.

(5): (±)-endo-2-Hydroxy-1,3,3-trimethyl-7-oxabicyclo[2.2.1]heptane ((±)-alpha-7-oxa-fenchol)

A 1M solution of lithium aluminum hydride in ether (15 ml., 0.015 moles) was added dropwise to a solution of (±)-1,3,3-trimethyl-7-oxabicyclo[2.2.1]heptane-2-one from step (4) (1.10 g, 0.006 moles) in 50 ml. of THF at 0° C. The reaction mixture was stirred for 30 minutes, and then quenched by the careful addition of saturated $Na_2SO_4$ solution. The resulting white precipitate was removed by vacuum filtration and washed with ether. The filtrate was evaporated, affording the product as a colorless oil which was characterized by NMR. Yield: 0.82 g.

c: o-Nitrophenylsulfonyl-D-phenylglycine-(±)-alpha-7-oxafenchyl ester

The purified o-Nps-D-phenylglycine from step 1a (1.44 g., 0.005 moles) and (±)-alpha-7-oxafenchol from step 1b (0.74 g., 0.005 moles) were dissolved in 50 ml. of $CH_2Cl_2$ and cooled to −65° C. N,N'-dicyclohexylcarbodiimide (1.00 g., 0.005 moles) was added and the mixture then stirred for 20 minutes. A catalytic amount of 4-dimethylaminopyridine (33 mg.) was added and then this reaction mixture was stirred at −65° C. for 1 hour. The reaction mixture was then gradually warmed to −23° C. ($CCl_4$/ice bath) and stirred for 3 hours. The mixture was then filtered and the filtrate washed successively with $H_2O$, 2% $Na_2CO_3$, $H_2O$, and brine. The washed filtrate was dried over $MgSO_4$, filtered and then concentrated to give the crude product. The crude product was purified by flash chromatography on silica gel using 25% ethyl acetate/hexane as the eluting solvent. The purified product was characterized by NMR. Yield: 1.18 g.

Step 2: D-Phenylglycine-(±)-alpha-7-oxa-fenchyl ester

The purified o-Nps-D-phenylglycine-(±)-alpha-7-oxa-fenchyl ester from step 1b (1.10 g., 0.0025 moles) was dissolved in 50 ml. of acetone and 5N HCl (0.5 ml.) was added. The reaction mixture was stirred for 15 minutes and then the acetone was evaporated. The residue was dissolved in 0.1N HCl, was extracted with ether to remove non-basic impurities and was then adjusted to pH 10 with NaOH. The alkaline solution was extracted with ethyl acetate 3 times. The combined extracts were successively washed with $H_2O$ and brine, dried over $MgSO_4$, and then evaporated to give the desired ester which was characterized by NMR. Yield: 0.55 g.

Step 3: beta-Benzyl-N-carbobenzyloxy-L-aspartyl-D-phenylglycine-(±)-alpha-7-oxa-fenchyl ester By a procedure similar to that of Example 1, Step 3, the ester from step 2 was converted to the diprotected L-aspartyl-D-phenylglycine-(±)-alpha-7-oxa-fenchyl ester. Yield: 0.91 g.

Step 4: alpha-L-Aspartyl-D-phenylglycine-alpha-7-oxa-fenchyl ester

By a procedure similar to that of Example 1, Step 4, the diprotected ester from step 3 was converted to a mixture of diastereomers from which the desired sweetener (either (+) or (−) oxa-fenchyl ester) was isolated by semi-preparative high performance liquid chromatography using a Whatman Magnum 9 ODS-3 column and 0.01M ammonium acetate in methanol/water (50/50), pH adjusted to 5.4 with acetic acid, as the eluting solvent. The sweetener identity was confirmed by NMR. Sweetness intensity: approximately 1000X based on informal panel testing.

The alpha-L-aspartyl-D-phenylglycine amides of the present invention can also be synthesized according to the previously described schemes for the esters by using a primary amine $R'NH_2$ instead of the alcohol. Amines $R'NH_2$ used in this synthesis can be obtained from the respective ketone 4 by the oxime procedure described in U.S. Pat. No. 4,411,925 to Brennan et al., issued Oct. 25, 1983 (herein incorporated by reference), especially column 12, line 55 to column 20, line 9, and Example 47. See also U.S. application Ser. No. 630,504 to John M. Janusz filed July 13, 1984 (Case 3293), Example 10, herein incorporated by reference, for the synthesis of an amide according to this reaction scheme.

The amides of the present invention can also be synthesized according to the following alternative 4-step reaction scheme:

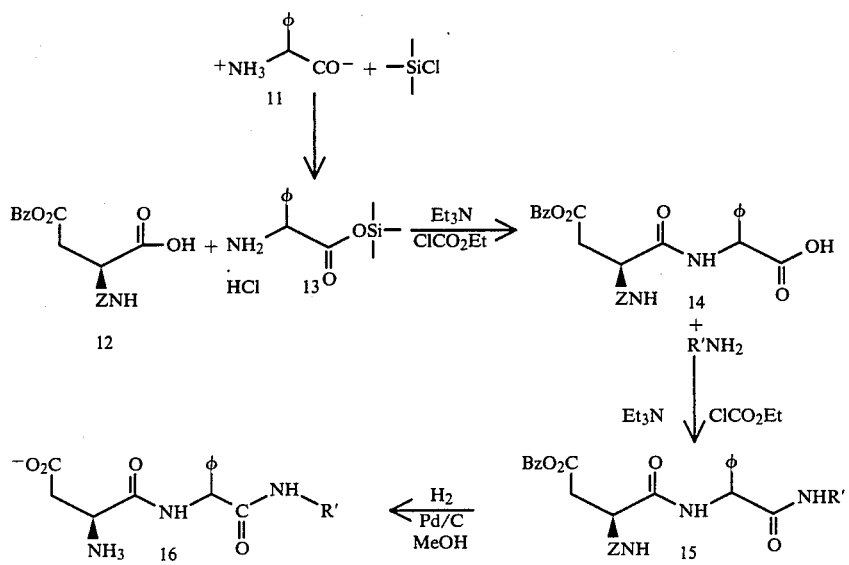

In the first step, D-phenylglycine 11 is reacted with trimethylsilylchloride to form the silyl ester 12. In the second step, silyl ester 12 is coupled to diprotected L-aspartic acid ester 13 using triethylamine and ethyl chloroformate to form diprotected amide 14. In the third step, amine R'NH$_2$ is coupled to diprotected amide 14 using triethylamine and ethyl chloroformate to form diprotected amide 15. In the fourth step, the protecting groups are removed by hydrogenation of amide 15 over palladium to yield sweetener 16. See U.S. application Ser. No. 630,504 to John M. Janusz filed July 13, 1984 (Case 3293), Example 12, herein incorporated by reference, for the synthesis of an amide according to this alternative reaction scheme.

The alpha-L-aspartyl-D-p-hydroxyphenylglycine esters of the present invention can be synthesized according to Example 13 of U.S. application Ser. No. 630,504 to John M. Janusz, filed July 13, 1084 (Case 3293), herein incorporated by reference.

D. Uses of alpha-L-aspartyl-D-phenylglycine esters and amides

The esters or amides of the present invention can be used to sweeten a variety of edible materials. Also, mixtures of these esters or amides with other sweeteners, in particular, mixtures of these esters or amides with saccharin or its non-toxic salts can be used. As used herein, "non-toxic salts of saccharin" means those salts of saccharin with physiologically acceptable cations such as sodium, potassium, calcium or ammonium. The mixtures of the present esters or amides with saccharin can be in a ratio (sweetness equivalent basis) of from about 2:1 to about 1:9, and preferably from about 1:1 to about 1:4. Mixtures of the present esters and amides with sweeteners other than saccharin can also be used.

Examples of such sweeteners include Acesulfam; the alpha-L-aspartyl-L-phenylalanine lower alkyl esters disclosed in U.S. Pat. No. 3,492,131 to Schlatter, issued Jan. 27, 1970 (herein incorporated by reference), in particular the methyl ester known as aspartame; the alpha-L-aspartyl-L-1-hydroxymethylalkyl amides disclosed in U.S. Pat. No. 4,338,346 to Brand, issued July 6, 1982 (herein incorporated by reference); the alpha-L-aspartyl-L-1-hydroxyethylalkyl amides disclosed in U.S. Pat. No. 4,423,029 to Rizzi, issued Dec. 27, 1983 (herein incorporated by reference); the alpha-L-aspartyl-D-alanine amides disclosed in U.S. Pat. No. 4,411,925 to Brennen et al., issued Oct. 25, 1983 (herein incorporated by reference); and the alpha-L-aspartyl-D-serine amides disclosed in U.S. Pat. No. 4,399,263 to Brennen et al., issued Aug. 16, 1983 (herein incorporated by reference). Low calorie mixtures can also be formulated which contain esters or amides of the present invention with sucrose.

The esters and amides of the present invention, including mixtures thereof with other sweeteners, are useful for sweetening a variety of food products, such as fruits, vegetables, juices, cereals, meat products such as ham or bacon, sweetened milk products, egg products, salad dressings, ice creams and sherbets, gelatins, icings, syrups, cake mixes and frostings. In particular, these sweeteners are useful for sweetening a variety of beverages such as lemonade, coffee, tea, and particularly carbonated beverages. The sweeteners of the present invention can also be used to sweeten dentifrices, mouthwashes, and chewing gums, as well as drugs such as liquid cough and cold remedies. As an alternative to direct addition of the esters and amides of the present invention to the foregoing edible materials, sweetner concentrates can be prepared using these esters and amides in, for example, granular or liquid form. These concentrates can then be conventionally metered into foods, beverages and the like as desired by the user.

The esters and amides of the present invention are stable substances that can be used in a variety of physical forms such as powders, granules, tablets, syrups, pastes, solutions and the like. Liquid or solid ingestible carriers such as water, glycerol, starch, sorbital, salts, citric acid, cellulose and other suitable non-toxic substances can also be used. These sweetening agents can be readily used in pharmaceutical compositions to impart a sweet taste.

The ester and amide sweeteners of the present invention are used in amounts sufficient to provide a sweet taste of the desired intensity for orally ingested products. The amount of the sweetener added will generally depend upon commercial needs as well as individual sweetness sensitivies.

Specific Embodiments of Oral Products Containing Alpha-L-Aspartyl-D-Phenylglycine Esters

A. Beverage

Mixtures of the alpha-7-oxa-fenchyl ester sweetener of Example 2 with other sweeteners are used in cola beverages that are formulated as follows:

| Ingredients | Embodiment 1 (%) | Embodiment 2 (%) |
|---|---|---|
| $H_3PO_4$ | 0.06 | 0.06 |
| Caramel color | 0.25 | 0.25 |
| Flavor | 0.0032 | 0.0032 |
| Saccharin | 0.020 | 0.011 |
| Aspartame | 0.005 | 0.015 |
| Fenchyl ester | 0.0005 | 0.0036 |
| $CO_2$ | 3.5 (volumes) | 3.5 (volumes) |

B. Toothpaste

The following toothpaste formulation is within the scope of the present invention:

| Ingredient | Wt. % |
|---|---|
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl cellulose | 1.20 |
| Sodium coconut alkyl sulfate (20% active) | 2.30 |
| Sodium fluoride | 0.22 |
| Sweetener (Example 2) | 0.016 |
| Flavor | 0.90 |
| Red urea formaldehyde agglomerates | 0.65 |
| Water and minor ingredients | Balance |

C. Mouthwash

A mouthwash according to the present invention is prepared by co-dissolving the following ingredients:

| Ingredient | Percent by Weight |
|---|---|
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent* | 0.02 |
| Water and minor ingredients | Balance |

*Sweetener of Example 2, Hydrochloride salt

D. Dentifrice

A gel dentifrice having the following formulation is prepared by conventional means:

| Ingredients | Percent by Weight |
|---|---|
| Silica xerogel | 12.00 |
| Silica aerogel | 5.00 |
| Hydroxyethyl cellulose | 1.50 |

| Ingredients | Percent by Weight |
|---|---|
| Glycerine | 34.76 |
| Stannous fluoride | 0.41 |
| Flavor (Wintergreen) | 0.95 |
| Color (FD&C Blue #1) | 0.03 |
| 21% sodium lauryl sulfate-79% glycerine mixture | 6.00 |
| Sweetener* | 0.012 |
| Water and minor ingredients | Balance |

*Example 2, Calcium salt.

The above composition is prepared by blending and deaerating the listed ingredients in standard fashion.

E. Chewing Gum

A chewing gum is prepared by replacing the sucrose normally added to chewing gum with the sweeteners of the present invention. A gum base is prepared from:

| Ingredients | Weight in Grams |
|---|---|
| 60% latex | 18 |
| Hydrogenated rosin esters | 44 |
| Paracumarine resin 7.5 | |
| Candellila wax | 6 |
| Glyceryl tristearate | 2.5 |
| Ethyl cellulose | 2 |
| Calcium carbonate | 20 |

The gum base is used with the sweeteners of the present invention to prepare a chewing gum having a greatly reduced sugar content.

| Ingredients | Percent by Weight |
|---|---|
| Gum base | 68 |
| Sweetener* | 0.6 |
| Corn syrup | 16 |
| Flavor | 1 |

*Example 2

Chewing gum can also be prepared using other sweeteners of the present invention.

F. Powdered Sweetener Concentrate

| | |
|---|---|
| Sweetener of Example 1, Hydrochloride Salt | 6.4 mg. |
| Dextrose | 840 mg. |

One packet containing the foregoing ingredients will be the approximate equivalent of two teaspoons of sugar.

H. Liquid Sweetener Concentrate

| | Gm. % |
|---|---|
| Example 2, Hydrochloride salt | 0.12 |
| Benzoic acid | 0.1 |
| Methyl paraben | 0.05 |
| Water | Balance |

Ten drops provides the approximate sweetening power of one teaspoon of sugar.

What is claimed is:

1. A compound of formula:

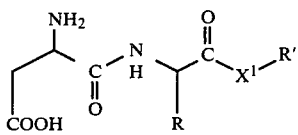

and non-toxic salts thereof; wherein the aspartyl portion of the compound has the L configuration and the phenylglycine portion has the D configuration; wherein $X^1$ is O or NH; wherein R is a phenyl group having the formula:

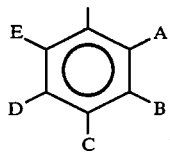

wherein A, B, C, D and E are H, OH, F, Cl, Br, or $C_1$-$C_4$ lower alkyl, hydroxy alkyl or alkoxy; and wherein R' is selected from the group consisting of bicyclic radicals having formulas (a) and (b):

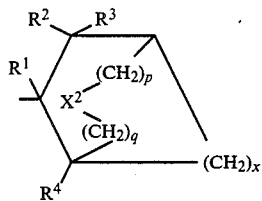

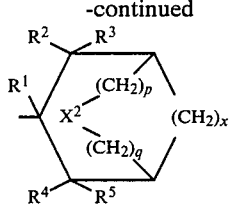

wherein $R^1$, $R^2$, $R^3$, $R^4$ and $R^5$ are H, or $C_1$-$C_4$ lower alkyl, hydroxyalkyl or alkoxy; provided that at least one of $R^2$, $R^3$, $R^4$ and $R^5$ is $C_1$-$C_4$ lower alkyl, hydroxyalkyl or alkoxy; $X^2$ is O; p and q are 0, 1, 2, or 3 and the sum or p+q is not greater than 3; x is 1, 2, or 3.

2. The compound of claim 1 wherein one of A, B, C, D and E is OH, the remainder being H.

3. The compound of claim 2 wherein C is OH and A, B, D and E are each H.

4. The compound of claim 1 wherein A, B, C, D and E are each H.

5. The compound of claim 1 wherein $X^1$ is O.

6. The compound of claim 1 wherein R' is alpha-7-oxa-fenchyl.

7. The compound of claim 1 wherein R' is beta-7-oxa-fenchyl.

8. A composition comprising:
(a) about 50% of the compound of claim 1; and
(b) the remainder being a compound of the formula:

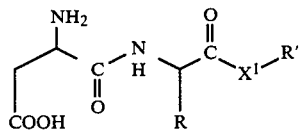

wherein the aspartyl and phenylglycine portions of the compound both have the L configuration.

9. A composition comprising the compound of claim 6 or 7 with a sweetener selected from the group consisting of saccharin and alpha-L-aspartyl-D-phenylalanine lower alkyl esters in a ratio of from about 2:1 to about 1:9 on a sweetness equivalent basis.

* * * * *